United States Patent [19]

Schmider et al.

[11] 4,225,234
[45] Sep. 30, 1980

[54] METHOD FOR SAMPLING IN FLAMELESS ATOMIC ABSORPTION SPECTROPHOTOMETRY

[75] Inventors: Paul Schmider, Munich; Wolfgang Ruberg, Ascheim, both of Fed. Rep. of Germany

[73] Assignee: Beckman Instruments GmbH, Munich, Fed. Rep. of Germany

[21] Appl. No.: 928,490

[22] Filed: Jul. 27, 1978

[30] Foreign Application Priority Data

Aug. 5, 1977 [DE] Fed. Rep. of Germany ....... 2735467

[51] Int. Cl.³ .............................................. G01J 3/30
[52] U.S. Cl. .................................................. 356/312
[58] Field of Search ........................................ 356/312

[56] References Cited

U.S. PATENT DOCUMENTS 3,788,752 1/1974 Slavin et al. ......................... 356/312

OTHER PUBLICATIONS

"Controlled Atmosphere Discontinuous Semiautomatic Dispenser for Carbon Rod Atomizer"; Sacchetti et al.; Analytical Chemistry, vol. 48#8 Jul. 1976 pp. 1175-1177.

Primary Examiner—Vincent P. McGraw
Attorney, Agent, or Firm—R. J. Steinmeyer; Robert R. Meads; John R. Shewmaker

[57] ABSTRACT

A method of flameless atomic absorption analysis in which an element in a sample is measured by vaporizing the sample in a graphite crucible or cuvette and measuring the absorbance of the atomic vapor at a wavelength characteristic of the element. The method includes the steps of (1) successively introducing a preselected number of aliquots of the same sample into the graphite cuvette, (2) thermally pretreating each sample aliquot upon introduction to remove volatile or decomposable substances therefrom, and (3) vaporizing sample remaining in the cuvette for measurement only after performing the predetermined successive number of sample introduction and thermal pretreatment cycles.

1 Claim, 5 Drawing Figures 1-fold sample application of 10 μl of a 0,05 ppm Cu-solution
2-fold sample application of 10 μl of a 0,05 ppm Cu-solution
3-fold sample application of 10 μl of a 0,05 ppm Cu-solution
4-fold sample application of 10 μl of a 0,05 ppm Cu-solution
5-fold sample application of 10 μl of a 0,05 ppm Cu-solution

METHOD FOR SAMPLING IN FLAMELESS ATOMIC ABSORPTION SPECTROPHOTOMETRY

BACKGROUND OF THE INVENTION

1. Field of the Invention

The invention relates to a method of sampling in flameless atomic absorption spectrophotometry.

2. Description of the Prior Art

Atomic absorption analysis is a method for the quantitative determination of an element in a sample to be analyzed and is based on measurement of the optical attenuation of a beam of atomic resonance radiation by atoms of the element which are in the ground state.

The known atomic absorption spectral instruments include as an atomizing device an electrically heatable graphite cuvette into which the sample is introduced by way of a sample inlet either by hand or by an automatic pipette. The current flowing through the graphite tube is automatically controlled by a programmable control system, so that the sample, in accordance with a series of time-sequential steps is first dried, then ashed, and finally atomized (vaporized). This procedure of elemental quantitation in the graphite cuvette makes use of a limited amount of sample and vaporizes the sample completely. The dissolved sample must be introduced into the graphite tube in precisely known amount. A time-dependent analytical signal is measured, in which the time-variation of absorption depends on the state of the sample. According to the known prior state of the art, methods and apparatus are known for automatic sampling in flameless atomic absorption spectrophotometry, as described for example in publication No. 1419/3.76 by the company Bodenseewerk Perkin-Elmer, in which programmed control of the automatic analysis sequence permits repeated analyses of a sample having a known elemental content, in order to determine the precision of the measured value.

These prior known arrangements are not completely satisfactory, in that they have the disadvantage, when different sample volumes are to be used, that different settings must be made on the instrument or that the pump module must be changed. Also, the different liquid volumes in the graphite cuvette spread out in varying degree, and upon being atomized contribute in varying amount to the non-specific absorption. Moreover, the reproducibility of the measurements depends upon the sample volume such that relatively small sample volumes, which do not spread out in varying degree, usually provide better reproducibility.

SUMMARY OF THE INVENTION

The present invention resides in a method of conducting atomic absorption analysis which provides increased sensitivity in elemental measurements through the use of multiple (repeated) sampling in a manner which avoids excessive spreading of large liquid volumes and which insures that the non-specific light absorption at the end of the sampling cycle is the same as or close to that for a smaller amount of sample.

According to the invention, these problems are solved by conducting a preselected number of automatic, multiple (repeated) samplings of one and the same sample batch, each sampling being followed by a programmable thermal pretreatment of the sample aliquot until, on completion of the preselected number of sampling and pretreatment cycles, atomization (vaporization) is initiated for the measurement process per se, and such that the analytical signal resulting from this measuring process is proportional to the product of the amount of the element being determined and the number of sampling cycles. The thermal pretreatment providing drying and subsequent ashing as required is continued only to the point of removing substances, such as solvent, water crystallization, and inorganic and organic matrix materials, which unavoidably accompany the element to be determined. This pretreatment is fitted into the sampling scheme in such a way that none of the sample substance is lost, and can for example be repeated five times, with the result in this case that the sensitivity of an individual measurement with the reduced load of matrix material in the graphite cuvette can be increased up to five-fold in value. The advantage in this procedure is that the same sample volume introduced each time into the graphite tube always spreads out in equal degrees, and that excessive spreading caused by larger volumes of liquids is avoided. The effect of the thermal pretreatment is that the element to be determined is confined to an almost immeasurably small volume, and that the matrix components still remaining are reduced to a minimum. In this way, the non-specific light absorption at the end of the sampling cycle for most matrices is the same for a large quantity of sample as for a smaller quantity.

The basic concept of the invention is applicable in all cases where flameless atomic absorption spectrophotometry is used to determine trace elements in a sample solution.

The invention is also well adapted for constructing a calibration curve from a standard solution having a known elemental content by varying the number of sampling steps. In this way, the dilution errors are eliminated that may occur when standard samples are made up in different elemental concentrations and the precision of measurement is thereby increased.

DESCRIPTION OF THE PREFERRED EMBODIMENT

Figure 1:
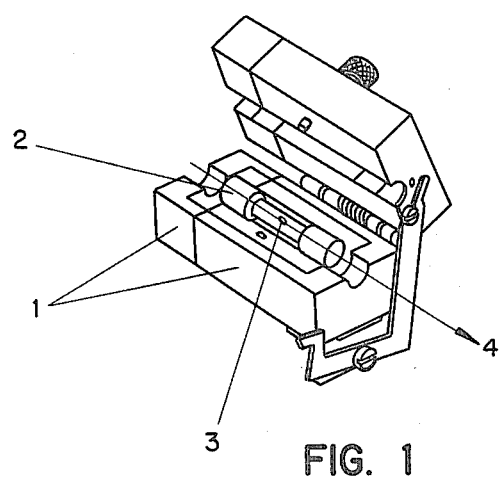
FIG. 1 is a perspective view of a graphite cuvette for use in a flameless atomic absorption spectometer.

According to FIG. 1, the graphite cuvette is of the usual construction and includes water-cooled electrodes 1 connected to the ends of the graphite tube 2, the latter having a sample inlet 3 opening into a heating zone and being traversed longitudinally with a light beam, indicated by arrow 4, for carrying out the atomic absorption measurement. The graphite tube 2 is flushed internally and externally with inert gas, so as to avoid burning of the graphite tube 2.

Figure 2:
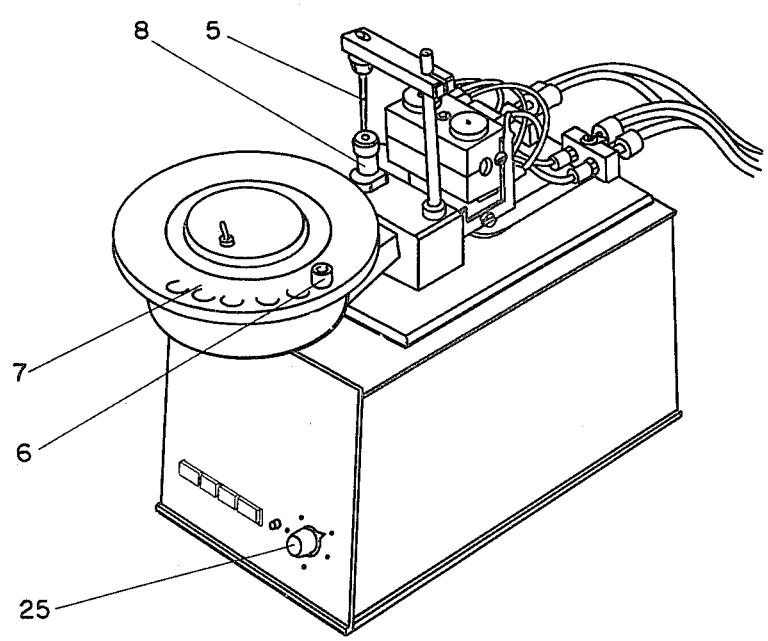
FIG. 2 is a perspective view of an automatic sampling system incorporating the cuvette of FIG. 1.

According to the sampling system illustrated in FIG. 2 a small sample of about ten microliters is automatically picked up by a sampling tip 5 from a sample container 6 on the sample turntable 7. Following a swinging motion of the sampling tip 5 the sample is delivered into graphite tube 2. An air bubble is now drawn into the sampling tip 5 to separate the sample from the rinse liquid before the (next) sample is taken and the sampling tip 5 is flushed at the wash position 8.

Figure 3:
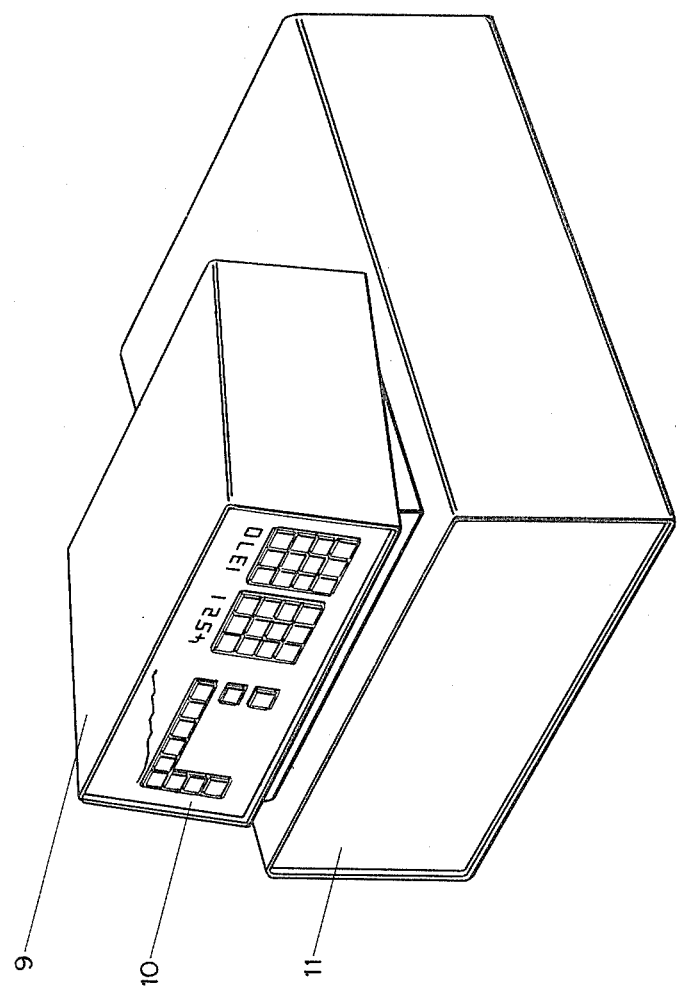
FIG. 3 is a perspective view of a current supply and control module for the sampling system of FIG. 2.

FIG. 3 illustrates a programmable digital control system that serves to control the above-described process as well as the heating level in the graphite cuvette. The upper portion 9 of the control system contains the control panel 10, the program memory and the sequence control for the analysis program. The lower section 11 houses the high current supply.

Figure 4:
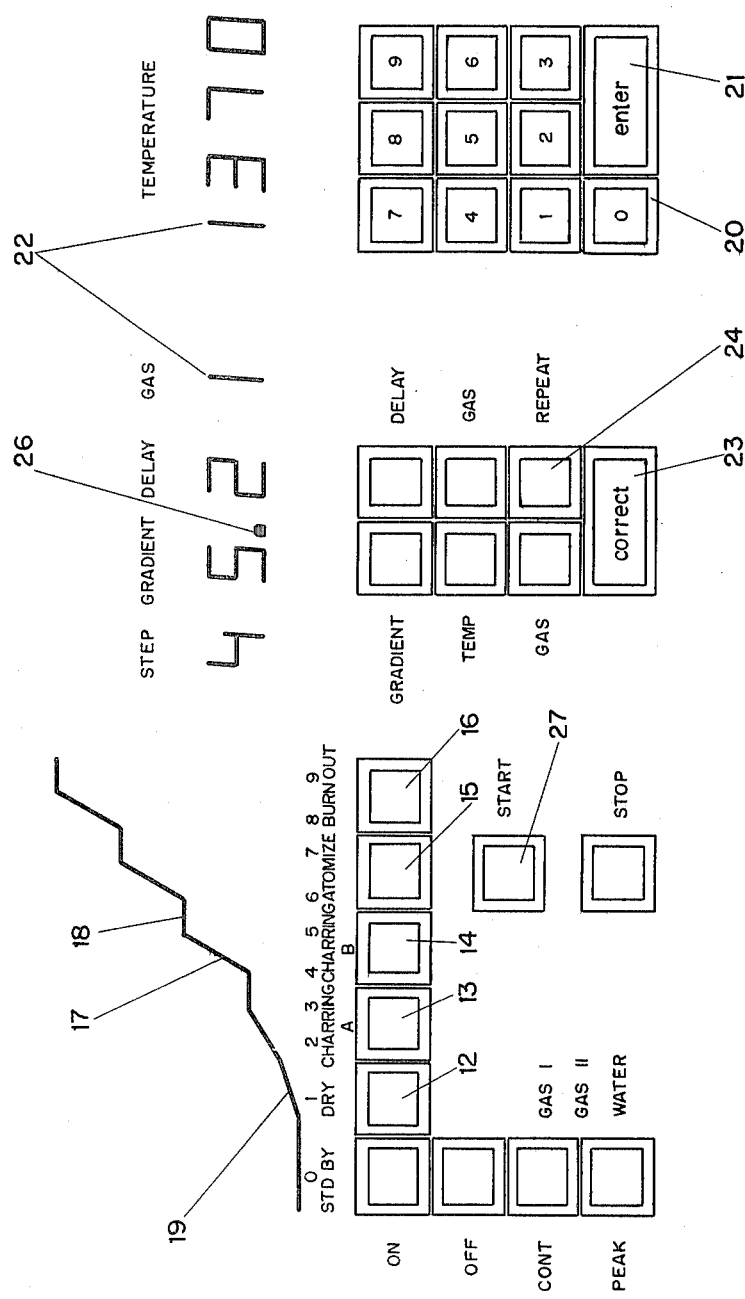
FIG. 4 is a front view of the control panel (with digital display) of the control module of FIG. 3.

As may be seen in FIG. 4 showing the control panel 10 of the control system, the analysis sequence comprises five principal program steps carried out in sequence, namely a drying step 12, ashing (A) 13, ashing (B) 14, atomizing 15, and burn-off. With the exception of the drying step 12, each of the five program steps includes a temperature ramp 17 and a temperature plateau 18, so that the total program sequence comprises nine separate steps. To make the course of this heating sequence visible, a graphic display 19 is mounted over the push buttons for these five principal program steps. The particular portion of this graphic display which is lighted at any moment corresponds to the process step in effect at that time. The numerical values for each of the temperature steps, as for example the slope of the temperature ramp, the plateau temperature, duration of the temperature plateaus, as well as the selected gas being used during the temperature ramp and plateau periods, are entered through a numeric keyboard 20 and upon pressing the button "Enter" 21 are transferred to memory. Simultaneously, the selected value appears on the digital display 22 as confirmation of the entry. Any of the program steps can be executed separately. Changes in the values can be entered into the program by pressing the "Correct" button 23.

By pressing button 24, a "Repeat" function can be programmed into the system for any of the program steps up to the end of the ashing (B) step 14. At this point, depending on the number of desired repetitions of thermal pretreatment, a number between 1 and 5 is programmed into the system. The "Repeat" function is corrolated in its action with switch 25 on the sampling system shown in FIG. 2, this switch being set for the selected number of sampling repetitions. As a result, the control system is conditioned to cause identical sample aliquots from the same sample container 6 to be introduced into the graphite cuvette a predetermined number of times. After each sample aliquot is introduced and before the next aliquot is introduced, the thermal pretreatment steps 12, 13, and 14 are performed. Each thermal pretreatment is continued only the point of removing volatile or decomposable substances, such as solvent, water crystallization, and inorganic and organic matrix materials, which unavoidably accompany the sample and the element to be determined. After each sampling and thermal pretreatment cycle, the pretreated sample remains within the graphite cuvette. The cuvette is then cooled, the next aliquot from the original sample is introduced into the cuvette, and thermal pretreatment steps 12, 13, and 14 are repeated. Accordingly, the heating program is automatically divided into the desired steps, and the graphite cuvette is cooled and prepared for the next sample addition, until the total preselected number of sampling and thermal pretreatment cycles has been completed. On completion of the sampling and thermal pretreatment cycles, the total analysis program is completed by then and only then performing the final atomization and burn-out steps. In this manner, atomization and quantitative measurement is then performed for the total quantity of thermally pretreated sample present in the cuvette from the predetermined number of prior successive sampling and thermal pretreatment cycles. In this way it becomes possible, for example, with five-fold sampling and thermal pretreatment to reduce the matrix loading in the graphite cuvette and to increase the sensitivity of a given determination by a factor of 5 without requiring any change in the apparatus. The preselected program step, up to the completion of the "Repeat" function, appears visually on the digital display 22 as the decimal point 26. Determinations made with a single sampling step are carried out when the number 0 is entered for the "Repeat" function.

The analysis sequence with or without the program "Repeat" function is triggered by pressing the "Start" button 27, and proceeds fully automatically. During the analysis process the system is locked against any programming entries, so that any accidental touching of the keyboard 20 will not result in any erroneous function. The program storage controls the value of the analytically significant parameters and announces any unallowable settings, as for example the use of a reactive gas in the atomizing stage, or atomization temperatures above 3500° C., by flashing indication on the display. Interruption of the inert gas supply or flow of the cooling water result in a termination of the program, and signalling of the source of failure by flashing of the display.

Figure 5:
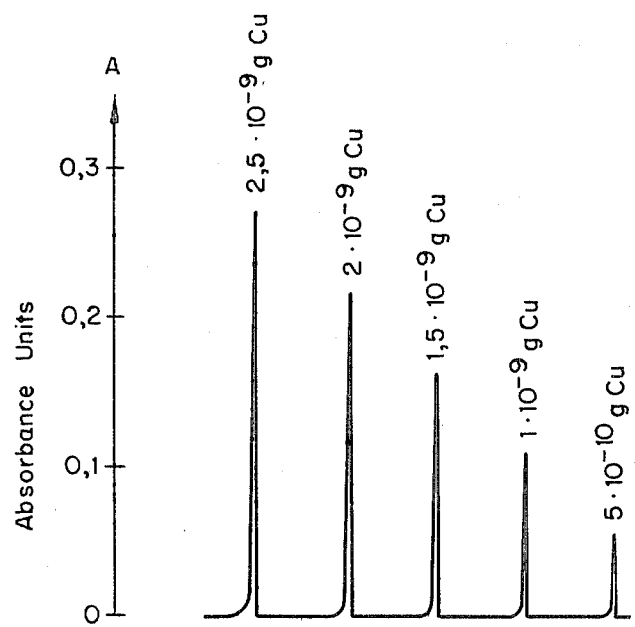
FIG. 5 is a Cu calibration curve obtained by multiple sampling.

FIG. 5 shows the result of atomic absorption spectrophotometric measurements on one- to five-fold samplings of a solution, each sampling 10 microliters of a 0.05 ppm of Cu solution in dilute hydrochloric acid. The result is a calibration curve obtained from a single standard solution.

A further advantage of the method of the invention is that a commercially available microprocessor, providing a coding function, can be conveniently used to control the complex program sequence.

It will be evident from the foregoing that the sampling and thermal pretreatment method of the invention avoids the excessive spreading caused by large sample volumes and enables the element to be measured to be confined to an almost immeasurably small volume with matrix components remaining therein reduced to a minimum. In this manner, non-specific light absorption at the end of the sampling cycle for most matrices is the same for a large sample quantity as for a smaller quantity. Moreover, while a preferred embodiment of the invention has been described, it will be apparent that modifications may be made therein without departing from the spirit and scope of the invention as defined by the appended claims.

What is claimed is:

1. In a method of performing atomic absorption analysis in which a sample solution is introduced into a heating zone and heated to vaporize the same for analysis which includes the steps of (a) introducing an aliquot of said sample solution into said heating zone, and (b) thermally pretreating the sample solution introduced in step (a) by heating the same in the heating zone to remove volatile or decomposable substances therefrom, the improvement comprising the further steps in combination of:
   (c) repeating steps (a) and (b) a preselected number of times for a preselected number of further aliquots of the same sample solution but prior to each repetition of step (a) cooling the heating zone as heated for the preceding step (b); and
   (d) vaporizing sample remaining in the heating zone for analysis only after performing the repetitions recited in step (c) said preselected number of times.

* * * * *